US011680952B2

(12) United States Patent
Asakura et al.

(10) Patent No.: US 11,680,952 B2
(45) Date of Patent: Jun. 20, 2023

(54) APPARATUS AND METHOD FOR AUTOMATED ANALYSIS

(71) Applicant: JEOL Ltd., Tokyo (JP)

(72) Inventors: Makoto Asakura, Tokyo (JP); Mine Yamashita, Tokyo (JP)

(73) Assignee: JEOL Ltd., Tokyo (JP)

( * ) Notice: Subject to any disclaimer, the term of this patent is extended or adjusted under 35 U.S.C. 154(b) by 375 days.

(21) Appl. No.: 16/360,406

(22) Filed: Mar. 21, 2019

(65) Prior Publication Data

US 2019/0302138 A1 Oct. 3, 2019

(30) Foreign Application Priority Data

Mar. 30, 2018 (JP) .............................. JP2018-067959

(51) Int. Cl.
*G01N 35/10* (2006.01)
*G01N 35/02* (2006.01)
(Continued)

(52) U.S. Cl.
CPC ....... *G01N 35/1004* (2013.01); *G01N 35/025* (2013.01); *B08B 3/00* (2013.01);
(Continued)

(58) Field of Classification Search
CPC .... G01N 35/1004; G01N 35/025; G01N 1/14; G01N 35/02; G01N 35/00584;
(Continued)

(56) References Cited

U.S. PATENT DOCUMENTS 6,003,531 A * 12/1999 Kimura .............. G01N 35/1004
  134/155
9,897,622 B2 * 2/2018 Horiuchi ............ G01N 35/1004
(Continued)

FOREIGN PATENT DOCUMENTS

EP 2407791 A1 1/2012
JP 62242858 A * 10/1987 ......... G01N 35/1004
(Continued)

OTHER PUBLICATIONS

Extended European Search Report issued in EP19165233.8 dated Sep. 3, 2019.

*Primary Examiner* — P. Kathryn Wright
*Assistant Examiner* — Curtis A Thompson
(74) *Attorney, Agent, or Firm* — The Webb Law Firm

(57) ABSTRACT

Described is an automated analyzer capable of effectively cleaning a dispensing probe without using a sweeping cleaning member. The automated analyzer includes: a receptacle holding portion for holding a plurality of receptacles in which aliquots of liquid are stored, an immersion cleaning solution holding portion for storing an immersion cleaning solution, an aliquot dispenser equipped with a drive mechanism for holding a dispensing probe operative to collect the aliquots of liquid from the receptacles, a measurement controller for controlling the drive mechanism and the dispensing probe such that the aliquots of liquid are successively collected at given cycles from the receptacles, and an immersion cleaning controller for controlling the drive mechanism and the dispensing probe such that an immersion cleaning operation is carried out for an immersion time that is at least twice as long as the period of each of the given cycles.

11 Claims, 10 Drawing Sheets

(51) Int. Cl.
   C12M 1/34      (2006.01)
   G01N 35/04     (2006.01)
   G01N 35/00     (2006.01)
   B08B 7/04      (2006.01)
   B08B 3/00      (2006.01)
   G01N 1/14      (2006.01)
   B32B 5/02      (2006.01)

(52) U.S. Cl.
   CPC .............. B08B 7/04 (2013.01); B32B 5/02 (2013.01); C12M 1/34 (2013.01); G01N 1/14 (2013.01); G01N 35/00 (2013.01); G01N 35/00584 (2013.01); G01N 35/02 (2013.01); G01N 35/04 (2013.01); G01N 35/10 (2013.01)

(58) Field of Classification Search
   CPC ........ G01N 35/04; G01N 35/00; G01N 35/10; G01N 2035/1006; B08B 3/00; B08B 7/04; B32B 5/02; C12M 1/34
   See application file for complete search history.

(56) References Cited

U.S. PATENT DOCUMENTS

| 10,695,803 B2* | 6/2020 | Gebauer ............. G01N 35/1004 |
| 2004/0054286 A1* | 3/2004 | Audain ............... B01F 11/0266 600/449 |
| 2011/0174343 A1* | 7/2011 | Azuma .............. G01N 35/1004 134/113 |
| 2011/0293474 A1* | 12/2011 | Sugimura .......... G01N 35/1004 422/62 |
| 2012/0318302 A1* | 12/2012 | Nakayama ................ B08B 3/08 134/26 |
| 2015/0204895 A1* | 7/2015 | Yasui ................. G01N 35/1004 422/64 |
| 2015/0293135 A1* | 10/2015 | Yamashita ....... G01N 35/00722 702/184 |
| 2017/0153263 A1* | 6/2017 | Mizuki .................. G01N 35/10 |

FOREIGN PATENT DOCUMENTS

| JP | 2014178267 A | 9/2014 |
| JP | 2014235001 A | 12/2014 |

* cited by examiner

FIG.5

OPERATIONAL SETTING FOR IMMERSION CLEANING OF PROBE

| | | UNIT | POSITION |
|---|---|---|---|
| (1) | CLEANING POSITON | PROBE CLEANING DEVICE | --- |
| (2) | IMMERSION DEPTH | 50 | mm |
| (3) | IMMERSION TIME | 300 | sec |

FIG.6

OPERATIONAL SETTING FOR IMMERSION CLEANING OF PROBE

| | | UNIT | POSITION |
|---|---|---|---|
| (1) | CLEANING POSITON | SAMPLE TURNTABLE | 1 |
| (2) | IMMERSION DEPTH | 50 | mm |
| (3) | IMMERSION TIME | 300 | sec |

MANUAL SETTING FOR IMMERSION CLEANING OF PROBE

AUTOMATIC EXECUTION SETTING
FOR IMMERSION CLEANING OF PROBE

|  | (1) EXECUTION TIMING | (2) INTERRUPTION OF NORMAL MEASUREMENT OPERATION |
|---|---|---|
| SETTING 1 | WHENEVER ASPIRATION FROM LOWER END OF ANALYTE PROBE IS CARRIED OUT 40 TIMES | YES |
| SETTING 2 | WHENEVER MEASUREMENT OF HbA1c IS PERFORMED 30 TIMES | NO |
| SETTING 3 | EVERY 24 HOURS | YES |

FIG.9

HISTORY OF EXECUTION OF IMMERSION CLEANING OF PROBE

| DATE AND TIME | INSTRUCTION FOR EXECUTION | CIRCUMSTANCES OF EXECUTION |
|---|---|---|
| 2017/11/24 10:13 | AUTOMATIC EXECUTION : SETTING2 | PERFORMED |
| 2017/11/24 15:36 | MANUAL EXECUTION | PERFORMED |
| 2017/11/25 15:36 | AUTOMATIC EXECUTION : SETTING3 | PERFORMED |
| 2017/11/26 15:36 | AUTOMATIC EXECUTION : SETTING3 | SHORTAGE OF IMMERSION CLEANING SOLUTION |
| 2017/11/27 09:58 | AUTOMATIC EXECUTION : SETTING2 | PERFORMED |
| 2017/11/27 13:02 | AUTOMATIC EXECUTION : SETTING1 | CANCELED |
| 2017/11/27 16:47 | MANUAL EXECUTION | PERFORMED |
|  |  |  |
|  |  |  |

FIG.10

HISTORY OF ALARM

| DATE AND TIME | ALARM No. | DETAILS |
|---|---|---|
| 2017/11/24 10:09 | 13474 | IMMERSION CLEANING IS IMMPOSSIBLE. |
| 2017/11/24 10:36 | 13422 | CLOT HAS BEEN DETECTED DURING ASPIRATING ANALYTE. |
| 2017/11/24 14:03 | 13842 | THE REST OF THE NUMBER OF TEST IS SLIGHTLY REMAINING. |
| 2017/11/24 14:42 | 13821 | REAGENT IS EXHAUSTED. |
| 2017/11/26 15:36 | 13475 | THERE IS A SHORTAGE OF IMMERSION CLEANING SOLUTION. |
| 2017/11/27 07:02 | 13808 | THERE IS A SHORTAGE OF BUFFER SOLUTION. |
|  |  |  |
|  |  |  |
|  |  |  |

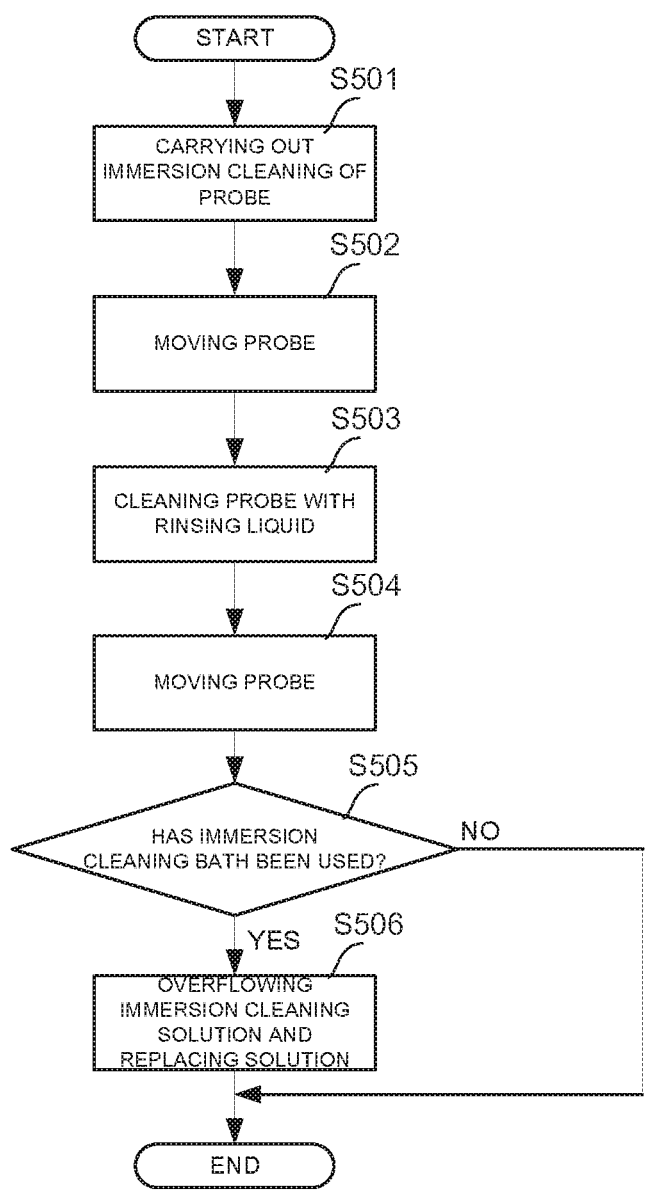

APPARATUS AND METHOD FOR AUTOMATED ANALYSIS

CROSS-REFERENCE TO RELATED APPLICATION

This application claims priority to Japanese Patent Application No. 2018-067959 filed Mar. 30, 2018, the disclosure of which is hereby incorporated by reference in its entirety.

BACKGROUND OF THE INVENTION

Field of the Invention

The present invention relates to an apparatus and method for automated analysis.

Description of Related Art

Biochemical analyzers for analyzing biochemical components contained in an analyte such as blood or urine are known as one type of automated analyzer. In such a biochemical analyzer, proteins and lipins contained in an analyte under analysis easily tend to adhere to a dispensing probe that collects the analyte. This raises the concern that there may occur carryover between analytes and consequent contamination of the analytes.

Accordingly, there has been proposed an automated analyzer equipped with a nozzle cleaning mechanism for wiping a sample dispensing nozzle (corresponding to the aforementioned dispensing probe) a preset number of times with a cleaning member while varying the position of the cleaning member at which it is pressed against the dispensing nozzle (see JP-A-2014-178267).

In recent years, an instrument for measuring HbA1c (hemoglobin A1c) has been placed as the above-described automated analyzer on the market. In this instrument, blood cells made to settle at the lowermost layer of the analyte by centrifugal separation are collected as a sample for measurement and, therefore, it is needed to insert a dispensing probe into the lower end of the analyte receptacle. Consequently, the tip of the dispensing probe is deeply immersed in the analyte. This presents the problem that a wide area of the outer wall of the dispensing probe is liable to become fouled. In the automated analyzer equipped with the above-described nozzle cleaning mechanism, however, the wiping cleaning member needs to be replaced and so there is the anxiety that the running costs may be increased.

SUMMARY OF THE INVENTION

Accordingly, it is an object of the present invention to provide an apparatus and method for automated analysis capable of effectively cleaning a dispensing probe without using any wiping cleaning member, resulting in reduced running costs.

This object is achieved in accordance with the teachings of the present invention by an automated analyzer comprising:

a receptacle holding portion for holding a plurality of receptacles in which aliquots of liquid are stored;

an immersion cleaning solution holding portion for storing an immersion cleaning solution;

an aliquot dispenser equipped with a drive mechanism for holding a dispensing probe operative to collect the aliquots of liquid from the receptacles held to the receptacle holding portion such that the dispensing probe can be moved between the receptacle holding portion and the immersion cleaning solution holding portion;

a measurement controller for controlling the drive mechanism of the aliquot dispenser and the dispensing probe such that the aliquots of liquid are successively collected at given cycles from the receptacles held to the receptacle holding portion; and an immersion cleaning controller for controlling the drive mechanism of the aliquot dispenser and the dispensing probe such that an immersion cleaning operation in which the dispensing probe is immersed in the immersion cleaning solution stored in the immersion cleaning solution holding portion is carried out for an immersion time that is at least twice as long as the period of each of the given cycles.

The present invention also provides a method of automated analysis using this automated analyzer.

According to the present invention, the dispensing probe can be effectively cleaned without using a wiping cleaning member. Consequently, an automated analyzer and automated analysis method capable of resulting in decreased running costs can be obtained.

BRIEF DESCRIPTION OF THE DRAWINGS

FIGS. 5 and 6 are diagrams illustrating different operational settings for immersion cleaning of a probe.

FIG. 9 is a diagram illustrating one example of the history of execution of immersion cleaning of a probe.

FIG. 10 is a diagram illustrating one example of the operational history of an alarm.

FIG. 13 is a flowchart illustrating a procedure of immersion cleaning of a probe used in the method of automated analysis illustrated in FIGS. 11 and 12.

DESCRIPTION OF THE INVENTION

Embodiments of the apparatus and method for automated analysis of the present invention are hereinafter described in detail with reference to the drawings.

<<Automated Analyzer>>

Figure 1:
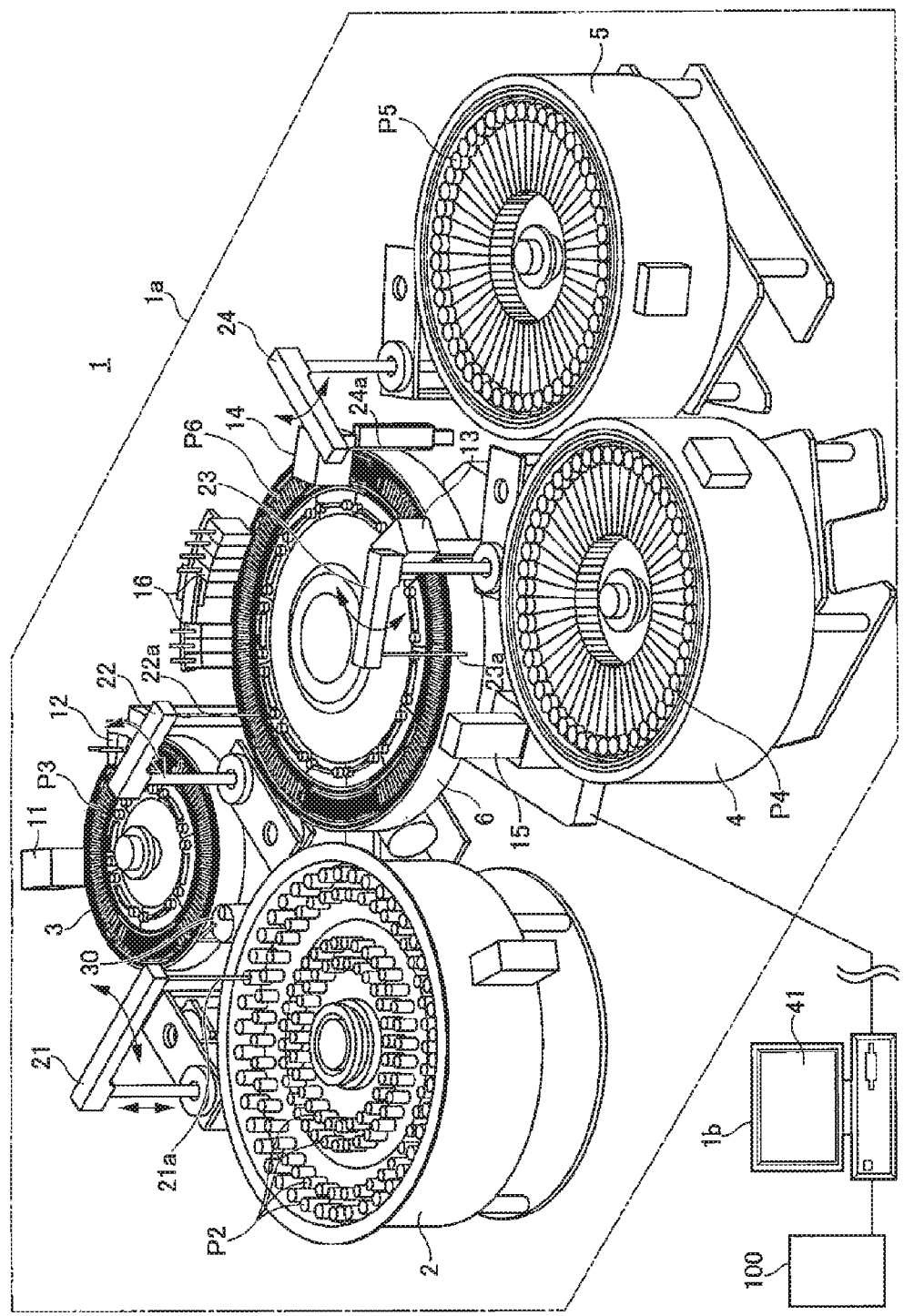
FIG. 1 is a schematic perspective view of an automated analyzer associated with one embodiment of the present invention.

FIG. 1 schematically shows the configuration of an automated analyzer associated with one embodiment of the present invention. This automated analyzer, 1, according to the present invention is a biochemical analyzer for analyzing biological components contained in each analyte such as blood or urine. As shown in FIG. 1, the automated analyzer 1 has a measuring section 1*a* and a control section 1*b*.

The measuring section 1*a* includes, for example, a sample turntable 2, a dilution turntable 3, a first reagent turntable 4, a second reagent turntable 5, and a reaction turntable 6. Furthermore, the measuring section 1*a* includes a dilution stirrer 11, a dilution cleaning device 12, a first reaction stirrer 13, a second reaction stirrer 14, a multi-wavelength photometer 15, and reaction receptacle cleaning devices 16. Additionally, the automated analyzer 1 includes an analyte dispenser 21, a diluted analyte dispenser 22, a first reagent dispenser 23, a second reagent dispenser 24, and a probe cleaning device 30. Further, the analyzer may include a cleaned receptacle holding portion (not shown).

On the other hand, the control section 1b includes a display device 41. Furthermore, the control section 1b has an input section, a data storage section, and a control unit which will be described in further detail hereinafter. First, the measuring section 1a and the control section 1b are described in turn.

<Measuring Section 1a>

Sample Turntable 2

The sample turntable 2 is one of holding portions for holding a plurality of receptacles in which liquid aliquots are stored. Plural rows of analyte receptacles P2 are held along the fringes of the sample turntable 2. The held analyte receptacles P2 are transported in both directions circumferentially. The sample turntable 2 is supported so as to be rotatable circumferentially by a drive mechanism (not shown). Analytes under measurement and control analytes used for accuracy management are stored as liquid aliquots in the analyte receptacles P2 which are held on the sample turntable 2. These various analytes under measurement are held in position on the sample turntable 2.

Diluent receptacles storing a diluent and immersion cleaning solution receptacles storing an immersion cleaning solution L1, to be described hereinafter, may be held on the sample turntable 2, as well as the analyte receptacles P2. It is assumed that the immersion cleaning solution receptacles in which the immersion cleaning solution L1 is stored are substantially of the same size either as an immersion cleaning bath 32 of the probe cleaning device 30, to be described below, or as each analyte receptacle P2. The sample turntable 2 described thus far may have a function of cooling the held analyte receptacles P2 and other receptacles.

Dilution Turntable 3

The dilution turntable 3 is one of the holding portions for holding a plurality of receptacles in which liquid aliquots are stored. The dilution turntable 3 holds along its fringes a plurality of dilution receptacles P3 and transports the held dilution receptacles P3 in both directions circumferentially. The dilution turntable 3 is supported so as to be rotatable circumferentially by a drive mechanism (not shown). Analytes aspirated from the analyte receptacles P2 arranged on the sample turntable 2 are diluted and dispensed as diluted analytes (liquid aliquots) into the dilution receptacles P3 held on the dilution turntable 3. The automated analyzer 1 may not be equipped with the dilution turntable 3.

First Reagent Turntable 4 & Second Reagent Turntable 5

The first reagent turntable 4 holds along its fringes a plurality of first reagent receptacles P4 and conveys the held first reagent receptacles P4 in both directions circumferentially. The second reagent turntable 5 holds along its fringes a plurality of second reagent receptacles P5 and conveys the held second reagent receptacles P5 in both directions circumferentially. The first reagent turntable 4 and the second reagent turntable 5 are holding portions for holding a plurality of receptacles in which liquid aliquots are stored. The first reagent turntable 4 and the second reagent turntable 5 are supported so as to be rotatable circumferentially by their respective drive mechanisms (not shown). A first reagent is dispensed from a reagent bottle as liquid aliquots into the first reagent receptacles P4 held on the first reagent turntable 4. A second reagent is dispensed from another reagent bottle as liquid aliquots into the second reagent receptacles P5 held on the second reagent turntable 5.

Reaction Turntable 6

The reaction turntable 6 is arranged among the dilution turntable 3, the first reagent turntable 4, and the second reagent turntable 5. The reaction turntable 6 holds along its fringes a plurality of reaction receptacles P6 and conveys the held reaction receptacle P6 in both directions circumferentially. The reaction turntable 6 is supported so as to be rotatable circumferentially by a drive mechanism (not shown). A given amount of a diluted analyte collected from a selected one of the dilution receptacles P3 on the dilution turntable 3 and a given amount of the first reagent collected from a selected one of the first reagent receptacles P4 on the first reagent turntable 4 or a given amount of the second reagent collected from a selected one of the second reagent receptacles P5 on the second reagent turntable 5 are dispensed into each of the reaction receptacles P6 held on the reaction turntable 6. In each reaction receptacle P6, the diluted analyte and the first reagent or the second reagent are stirred together, thus inducing a reaction. The reaction turntable 6 designed as described so far operates to maintain the temperature of the reaction receptacle P6 constant at all times by a thermostat bath (not shown). Where the automated analyzer 1 is not equipped with the dilution turntable 3, the analyte collected from the analyte receptacles P2 on the sample turntable 2 is dispensed as aliquots into the reaction receptacles P6 held on the reaction turntable 6.

Dilution Stirrer 11

The dilution stirrer 11 is disposed near the outer periphery of the dilution turntable 3 and has a stirring mechanism and a drive mechanism for driving the stirring mechanism. The dilution stirrer 11 inserts a stirring element (not shown) into a selected one of the dilution receptacles P3 held on the dilution turntable 3 and stirs together the analyte under measurement and the diluent.

Dilution Cleaning Device 12

The dilution cleaning device 12 is disposed near the outer periphery of the dilution turntable 3. The dilution cleaning device 12 is a device for cleaning the dilution receptacles P3 from which the diluted analyte has been aspirated by the diluted analyte dispenser 22, to be described hereinafter.

First Reaction Stirrer 13 & Second Reaction Stirrer 14

The first reaction stirrer 13 and the second reaction stirrer 14 are arranged around the reaction turntable 6. The first reaction stirrer 13 and the second reaction stirrer 14 stir together the diluted analyte and the first reagent or the second reagent, respectively, in the reaction receptacles P6 held on the reaction turntable 6. Each of the first reaction stirrer 13 and the second reaction stirrer 14 has a stirring mechanism and a drive mechanism for driving the stirring mechanism, and inserts a stirring element (not shown) into the reaction receptacle P6 held in position on the reaction turntable 6, and stirs together the diluted analyte (or analyte) and the first reagent or second reagent. Consequently, the reaction of the diluted analyte with the first reagent or the second reagent is promoted.

Multi-Wavelength Photometer 15

The multi-wavelength photometer 15 is a measuring section and disposed opposite to the outer peripheral wall of the reaction turntable 6. The multi-wavelength photometer 15 performs optical measurements on diluted analytes which have reacted with the first or second reagent in the reaction receptacles P6, outputs signals indicative of the amounts of various components in the analytes as absorbances, and detects the state of reaction of the diluted analytes.

Reaction Receptacle Cleaning Devices 16

The reaction receptacle cleaning devices 16 are arranged around the reaction turntable 6. The cleaning devices 16 are devices for cleaning the insides of the reaction receptacles P6 for which testing has been completed.

Analyte Dispenser 21

The analyte dispenser 21 is equipped with an analyte probe 21a that is a dispensing probe in the form of a thin tube. The analyte dispenser 21 is disposed near the outer peripheries of the sample turntable 2 and of the dilution turntable 3. The analyte dispenser 21 inserts the tip of the analyte probe 21a whose axial direction is kept vertical into the analyte in a selected one of the analyte receptacles P2 held on the sample turntable 2 by a drive mechanism (not shown) in accordance with a preset measurement program and draws a given amount of analyte into the analyte probe 21a. At this time, the sample turntable 2 transports the analyte receptacles P2 held in position on the sample turntable 2 into a given analyte collection position in accordance with the preset measurement program.

Furthermore, the analyte dispenser 21 inserts the tip of the analyte probe 21a into a selected one of the dilution receptacles P3 on the dilution turntable 3 and dispenses the analyte aspirated in the analyte probe 21a and a given amount of diluent (e.g., physiological salt solution) supplied from the analyte dispenser 21 itself into the dilution receptacle P3. Consequently, in the dilution receptacle P3, the analyte under measurement is diluted by a given dilution factor up to a desired concentration.

Where the automated analyzer 1 is not equipped with the dilution turntable 3, the analyte dispenser 21 inserts the tip of the analyte probe 21a into the reaction receptacle P6 on the reaction turntable 6. Then, the dispenser 21 dispenses the analyte drawn in the analyte probe 21a and a given amount of diluent (e.g., physiological salt solution) supplied from the analyte dispenser 21 itself into the reaction receptacle P6.

The analyte probe 21a is equipped with a liquid level detecting mechanism (not shown). The liquid level detecting mechanism acts to detect the heightwise position of the liquid level relative to the tip of the analyte probe 21a, for example, by utilizing the electrostatic capacitance between the liquid level and the tip of the analyte probe 21a.

Diluted Analyte Dispenser 22

The diluted analyte dispenser 22 is equipped with a diluted analyte probe 22a being is a dispensing probe in the form of a thin tube, and is disposed between the dilution turntable 3 and the reaction turntable 6. The diluted analyte dispenser 22 causes a drive mechanism (not shown) to insert the tip of the diluted analyte probe 22a having its axial direction kept vertical into a selected one of the dilution receptacles P3 on the dilution turntable 3 in accordance with a preset measurement program and draws in a given amount of diluted analyte from the tip of the diluted analyte probe 22a filled with the diluent through an air reservoir. Furthermore, the diluted analyte dispenser 22 inserts the tip of the diluted analyte probe 22a into a selected one of the reaction receptacles P6 on the reaction turntable 6 and dispenses the aspirated diluted analyte drawn in the diluted analyte probe 22a into the reaction receptacle P6. Where the automated analyzer 1 is not equipped with the dilution turntable 3, the analyzer 1 does not need to have the diluted analyte dispenser 22.

First Reagent Dispenser 23

The first reagent dispenser 23 is equipped with a first reagent probe 23a being a dispensing probe in the form of a thin tube, and is disposed between the reaction turntable 6 and the first reagent turntable 4. The first reagent dispenser 23 causes a drive mechanism (not shown) to insert the tip of the first reagent probe 23a having its axial direction kept vertical into a selected one of the first reagent receptacles P4 on the first reagent turntable 4 in accordance with a preset measurement program such that a given amount of the first reagent is aspirated through an air reservoir from the tip of the first reagent probe 23a filled with the diluent. Furthermore, the first reagent dispenser 23 inserts the tip of the first reagent probe 23a into a selected one of the reaction receptacles P6 on the reaction turntable 6 and dispenses the first reagent drawn in the first reagent probe 23a into the reaction receptacle P6.

Second Reagent Dispenser 24

The second reagent dispenser 24 is equipped with the second reagent probe 24a being a dispensing probe in the form of a thin tube, and is disposed between the reaction turntable 6 and the second reagent turntable 5. The second reagent dispenser 24 causes a drive mechanism (not shown) to insert the tip of the second reagent probe 24a having its axial direction kept vertical into a selected one of the second reagent receptacles P5 on the second reagent turntable 5 in accordance with a preset measurement program such that a given amount of the second reagent is aspirated through an air reservoir from the tip of the second reagent probe 24a filled with the diluent. Furthermore, the second reagent dispenser 24 inserts the tip of the second reagent probe 24a into a selected one of the reaction receptacles P6 on the reaction turntable 6 and dispenses the second reagent drawn in the second reagent probe 24a into the reaction receptacle P6.

Probe Cleaning Device 30

The probe cleaning device 30 serves to provide immersion cleaning of the tip of the analyte probe 21a of the analyte dispenser 21, and is placed in the trajectory or path of movement of the analyte probe 21a. As an example, it is herein assumed that the probe cleaning device 30 is mounted in the path of movement of the analyte probe 21a, the path being between the sample turntable 2 and the dilution turntable 3.

Figure 2:
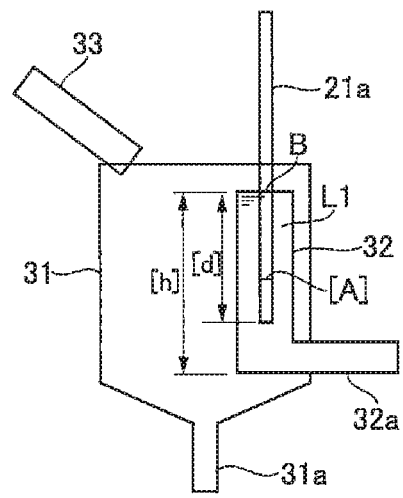
FIGS. 2 and 3 are side elevations of a probe cleaning bath mounted in the automated analyzer of FIG. 1, showing different operational states.
Figure 3:
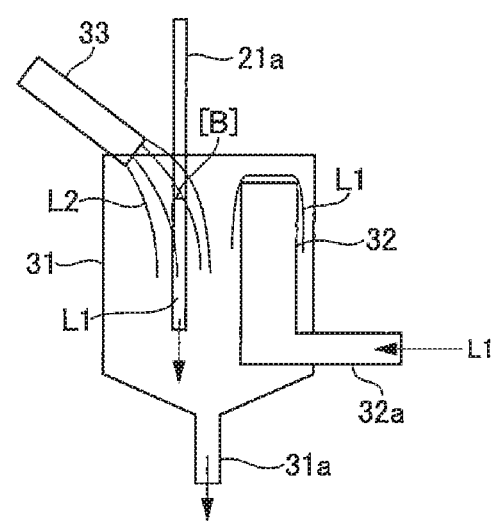

FIGS. 2 and 3 illustrate the configuration of the probe cleaning device 30 equipped to the automated analyzer 1 associated with the present embodiment. As shown in these figures, the probe cleaning device 30 has a cleaning bath 31, the immersion cleaning bath 32 mounted inside the cleaning bath 31, and a cleaning solution supply tube 33 positioned on the cleaning bath 31.

—Cleaning Bath 31—

The cleaning bath 31 is made of a cylinder having one end portion thereof constricted into a waste liquid tube 31a which is mounted to face downward.

—Immersion Cleaning Bath 32—

The immersion cleaning bath 32 is one of immersion cleaning solution holding portions in which the immersion cleaning solution L1 is stored. The immersion cleaning bath 32 is in the form of a cylinder having a diameter substantially permitting insertion of the tip of the analyte probe 21a, and is placed vertically within the cleaning bath 31. The lower end of the immersion cleaning bath 32 is brought as an immersion cleaning solution supply tube 32a out of the cleaning bath 31 and supplies the immersion cleaning solution L1 as a first cleaning solution into the immersion cleaning bath 32 from the immersion cleaning solution supply tube 32a. A flow rate adjusting device (not shown) is mounted as a drive mechanism in this immersion cleaning solution supply tube 32a to allow and stop the supply of the immersion cleaning solution L1.

The immersion cleaning solution L1 supplied from the immersion cleaning solution supply tube 32a into the immersion cleaning bath 32 is a drug solution for removing the analyte components adhering to the tip of the analyte probe 21a. This immersion cleaning solution L1 is a drug solution that exhibits effectiveness in removing the analyte. For example, if the analyte is blood, a drug solution that is effective in decomposing and removing proteins or deactivating them is used. In particular, hypochlorous-based drug solutions, acidic detergents, and alkali detergents can be used as the immersion cleaning solution L1.

The immersion cleaning bath 32 is so designed that the immersion cleaning solution L1 supplied from the immersion cleaning solution supply tube 32a into the immersion cleaning bath 32 overflows from above the immersion cleaning bath 32 and is discharged from the waste liquid tube 31a of the cleaning bath 31. Therefore, the top end of the immersion cleaning bath 32 is at a position lower than the top end of the cleaning bath 31.

As also shown in FIG. 2, it is assumed that the height [h] of the immersion cleaning bath 32 is such that the extent from the tip of the analyte probe 21a to the heightwise position [A] at which the analyte probe 21a is immersed in the analyte is sufficient to immerse the analyte probe 21a in the immersion cleaning solution L1 within the immersion cleaning bath 32. That is, it is assumed that the height [h] of the immersion cleaning bath 32 is such that the immersion depth [d] of the analyte probe 21a, i.e., the dimension of the portion of the analyte probe 21a that is immersed in the immersion cleaning solution L1 within the immersion cleaning bath 32, is much greater than the heightwise position [A] at which the analyte probe 21a is immersed in each analyte within the analyte receptacle P2. This immersion cleaning bath 32 may be comparable in size to, or greater than, each analyte receptacle P2. There may be plural immersion cleaning baths 32 inside the cleaning bath 31.

—Cleaning Solution Supply Tube 33—

The cleaning solution supply tube 33 supplies a shower of rinsing liquid L2 as a second cleaning solution onto the tip of the analyte probe 21a which is received in the cleaning bath 31 and outside the immersion cleaning bath 32. Especially, the cleaning solution supply tube 33 supplies the rinsing liquid L2 onto the analyte probe 21a from a position higher than the heightwise position [B] of the tip of the analyte probe 21a immersed in the immersion cleaning solution L1 within the immersion cleaning bath 32. This cleaning solution supply tube 33 has a drive mechanism consisting of a flow rate adjuster (not shown) to permit adjustment of the flow rate of the supplied rinsing liquid L2 as well as its stoppage.

Furthermore, the cleaning solution supply tube 33 is located off the immersion cleaning bath 32 and supplies a shower of rinsing liquid L2 from above the cleaning bath 31 into the cleaning bath 31. For example, it is assumed that the rinsing liquid L2 supplied from the cleaning solution supply tube 33 is pure water. The rinsing liquid L2 supplied from the cleaning solution supply tube 33 is discharged from the waste liquid tube 31a.

It is also assumed that probe cleaning devices (not shown) are mounted in the path of movement of the diluted analyte probe 22a of the diluted analyte dispenser 22, in the path of movement of the first reagent probe 23a of the first reagent dispenser 23, and in the path of movement of the second reagent probe 24a of the second reagent dispenser 24. Note these probe cleaning devices do not need to be identical in configuration to the above-described probe cleaning device 30. For example, they may not be equipped with the immersion cleaning bath 32 out of the component parts of the probe cleaning device 30.

Cleaned Receptacle Holding Portion

The measuring section 1a may be equipped with the cleaned receptacle holding portion (not shown) for holding immersion cleaned receptacles in which the immersion cleaning solution L1, to be described later below, is stored. It is assumed that the cleaned receptacle holding portion or portions are mounted in the path of movement of the analyte probe 21a. It is also assumed that the immersion cleaned receptacle held to this holding portion is comparable in size to the immersion cleaning bath 32 or each analyte receptacle P2. The cleaned receptacle holding portions for immersion cleaned receptacles may not be mounted in the automated analyzer 1 and may be mounted in plural locations.

<Control Section 1b>

Referring back to FIG. 1, the control section 1b is connected with drive mechanisms for various components of the above-described measuring section 1a and with the multi-wavelength photometer 15. Furthermore, the control section 1b is connected with an analyte supply device 100 for supplying analytes to the measuring section 1a.

Figure 4:
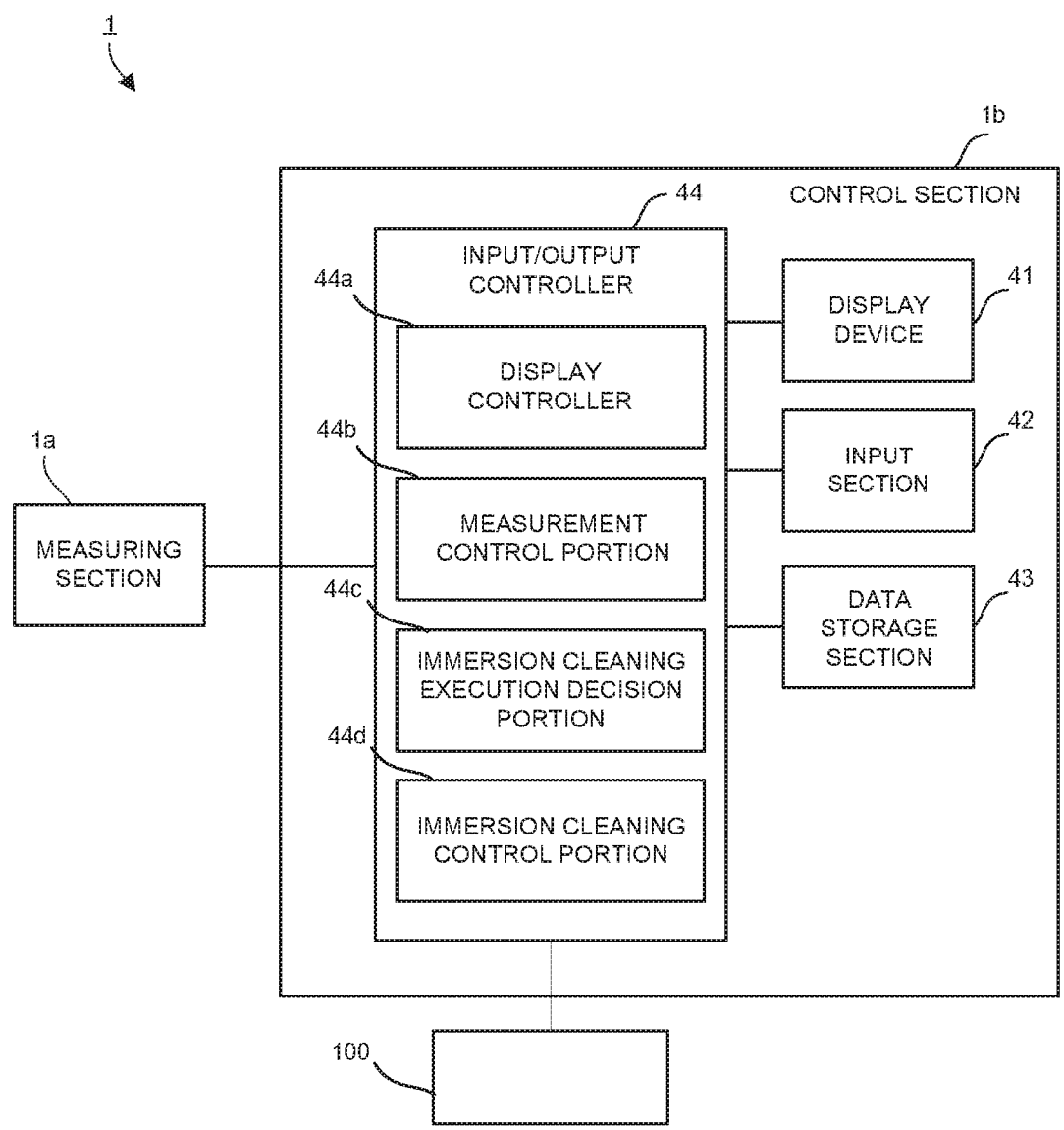
FIG. 4 is a block diagram of the automated analyzer of FIG. 1.

FIG. 4 is a block diagram of the automated analyzer 1 of the present embodiment. The configuration of the control section 1b shown in FIG. 4 is described also with reference to the previously referenced FIG. 1. As shown in FIG. 4, the control section 1b has the display device 41, an input section 42, a data storage section 43, and an input/output controller 44 whose configurations are described in detail as follows.

Display Device 41

The display device 41 displays the results of measurements performed by the multi-wavelength photometer 15. In addition, the display device 41 displays various setting information about the automated analyzer 1 and various history information. For example, a liquid crystal display is used as this display device 41. These various setting information and various history information include setting information and history information about immersion cleaning of the analyte probe as described later on. It is assumed that the display device 41 serves also as an alarm output portion to be described later. The alarm output portion is not restricted to the display device 41. The alarm output portion may also be a loudspeaker (not shown). The alarm output portion may consist of the display device 41 and a loudspeaker.

Input Section 42

The input section 42 accepts inputs regarding various settings made by the human operator of the automated analyzer 1 and other inputs, and outputs input signals to the input/output controller 44. For example, a mouse, a keyboard, a touch panel mounted on the display surface of the display device 41, or the like is used as the input section 42.

Data Storage Section 43

The data storage section 43 is made, for example, of a mass storage device such as a HDD (hard disk drive) or a semiconductor memory. Various programs executed by the input/output controller 44, to be described next, and the above-described various setting information and various history information are stored in this data storage section 43.

Input/Output Controller 44

The input/output controller 44 is made of a computing device such as a microcomputer. The computing device has storage sections such as a CPU (central processing unit), a ROM (read only memory), and a RAM (random access memory). The input/output controller 44 controls the operation of various internal portions of the automated analyzer 1. This input/output controller 44 has various portions such as a display controller 44a, a measurement control portion 44b, an immersion cleaning execution decision portion 44c, and an immersion cleaning control portion 44d. The storage sections such as the ROM and RAM may be the data storage section 43.

—Display Controller 44a—

The display controller 44a creates screens to be displayed on the display device 41 regarding the results of measurements performed by the multi-wavelength photometer 15, various setting information about the automated analyzer 1, and various history information. The various setting information and the various history information include setting information and history information regarding immersion cleaning of each analyte probe.

Specific examples of the screens created by the display controller 44a are described next with reference to FIGS. 5-10, which illustrate examples of setting information and history information regarding immersion cleaning of the analyte probe. The setting information regarding immersion cleaning of the analyte probe is based on inputs from the input section 42.

FIGS. 5 and 6 illustrate settings of operation for immersion cleaning of a probe, showing different operational states. One set of information of the settings regarding immersion cleaning of the analyte probe is an operational setting for immersion cleaning of the analyte probe as illustrated in these figures. The operational settings for immersion cleaning of the analyte probe include parameters: (1) cleaning position, (2) immersion depth, and (3) immersion time.

The (1) cleaning position is a position where the analyte probe 21a is subjected to an immersion cleaning process. In the example shown in FIG. 5, the probe cleaning device 30 is mounted in this cleaning position. In the example shown in FIG. 6, the cleaning position is the position 1 on the sample turntable 2 at which a selected one of the analyte receptacles P2 or other receptacle is held. This holding position is moved to a collection position in the orbit or path of movement of the analyte probe 21a by the drive mechanism that supports the sample turntable 2.

Where the automated analyzer 1 is equipped with the cleaned receptacle holding portion, the (1) cleaning position may be set on the cleaned receptacle holding portion.

The (2) immersion depth is the depth of the analyte probe 21a in the immersion cleaning solution L1. Referring to FIG. 2, it is assumed that the immersion depth [d] is set sufficiently greater than the heightwise position [A] at which the analyte probe 21a is immersed in the analyte within a selected one of the analyte receptacles P2. In the example shown in FIGS. 5 and 6, the immersion depth is set to 50 mm. That is, the analyte probe 21a is set to be immersed in the immersion cleaning solution L1 to a depth of 50 mm from the tip of the probe 21a.

The (3) immersion time is the time for which the analyte probe 21a is immersed in the immersion cleaning solution L1. During a normal measurement operation of the automated analyzer 1, let one cycle be the period from an operation for aspirating one analyte by means of the analyte probe 21a to an operation for aspirating a next analyte. This immersion time is characterized in that it is set to a time corresponding to 2 or more cycles. In the illustrated example, the immersion time is set to 300 seconds. If 1 cycle is 3 seconds, it follows that a time corresponding to 100 cycles is set as the immersion time.

Figures 7, 8:
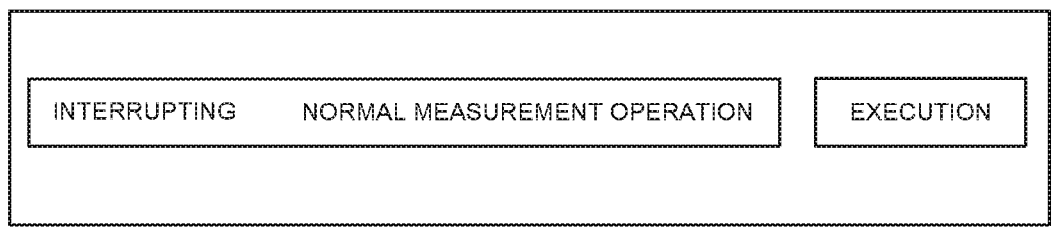
FIG. 7 is a diagram illustrating a manual execution setting for immersion cleaning of a probe.
FIG. 8 is a diagram illustrating an automatic execution setting for immersion cleaning of a probe.

FIG. 7 is a diagram illustrating a manual execution setting of probe immersion cleaning. Another piece of setting information regarding immersion cleaning of the analyte probe is the manual execution setting for probe immersion cleaning as illustrated in FIG. 7. This manual execution setting permits a human operator to carry out immersion cleaning of the analyte probe 21a at an arbitrary timing rather than a preset timing. For this manual execution setting for probe immersion cleaning, a choice screen is displayed to prompt the operator to make a decision as to whether or not the normal measurement operation is interrupted.

This choice screen displayed may include an execution button for carrying out probe immersion cleaning. Consequently, as described below in connection with the automated method of analysis, if the operator clicks on the execution button appearing on the display screen of the display device 41, for example, the process of the probe immersion cleaning may be progressed. This choice screen for manual execution setting for probe immersion cleaning may be included in a shutdown screen for normal measurement operation.

FIG. 8 is a diagram illustrating an automatic execution setting for probe immersion cleaning. A further piece of setting information regarding immersion cleaning of the analyte probe is the automatic execution setting for probe immersion cleaning as illustrated in FIG. 8. This automatic execution setting for probe immersion cleaning permits the analyte probe 21a to be immersion cleaned at a preset timing and has two operational choices: (1) execution timing and (2) interruption of normal measurement operation. The operator can specify plural settings including combinations of these choices by making inputs through the input section 42. All the specified settings are displayed on the display device 41 under control of the display controller 44a.

In the example shown in FIG. 8, there are three settings 1-3. In the settings 1, 2, and 3, immersion cleaning of the analyte probe 21a is automatically executed, respectively, whenever aspiration from the lower end of the analyte probe 21a is carried out 40 times, whenever measurement of HbA1c is performed 30 times, and when a period of 24 hours passes since the previous execution of immersion cleaning of the analyte probe 21a. This setting is not limited to a process in which operations are repeated or operations are performed repetitively at given intervals of time. For example, timing settings may be provided such that after execution of immersion cleaning of the analyte probe, given operations may be repeated a given number of times.

FIG. 9 is a diagram illustrating one example of the history of execution of immersion cleaning of the probe. One type of history information about immersion cleaning of the analyte probe is the history of execution of probe immersion cleaning as illustrated in FIG. 9. This history of execution of probe immersion cleaning is the history of probe immersion cleaning executed according to the above-described manual executing setting or automatic execution setting for the probe immersion cleaning. This execution history includes information about cancellation of probe immersion cleaning in a decision step performed by the immersion cleaning execution decision portion 44c to be described hereinafter.

FIG. 10 is a diagram illustrating one example of the operational history of an alarm. As a further type of history information about immersion cleaning of the analyte probe there is the operational history shown in FIG. 10. The operational history of the alarm is the history of alarm output during normal measurement operation or other operation of the automated analyzer 1 and includes the history of alarm output when immersion cleaning of the analyte probe is carried out.

—Measurement Control Portion 44b—

Referring back to FIG. 4, the measurement control portion 44b controls the operational timing of the various drive mechanisms constituting the measuring section 1a and the measurement timings of light intensity at the multi-wavelength photometer 15. The measurement control portion 44b controls the analyte dispenser 21 such that analytes are successively collected at certain cycles from the plurality of analyte receptacles P2 held on the sample turntable 2. Furthermore, the measurement control portion 44b controls the various drive mechanisms such that the analytes in the analyte receptacles P2 held on the sample turntable 2 are diluted to a given concentration, then first and second reagents are mixed and reacted with the diluted analytes, and the absorbances of the resulting reaction liquids are measured.

—Immersion Cleaning Execution Decision Portion 44c—

When the normal measurement operation or a terminating operation of the measuring section 1a is performed, the immersion cleaning execution decision portion 44c makes a decision as to whether immersion cleaning of the analyte probe is carried out. If the cleaning is carried out, the decision portion 44c instructs the immersion cleaning control portion 44d to carry out immersion cleaning of the analyte probe. Where immersion cleaning of the analyte probe cannot be carried out, the decision portion 44c instructs the alarm output portion to produce an alarm output.

This immersion cleaning execution decision portion 44c carries out these decisions and instructions based on the setting information stored in the data storage section 43, on a signal from a liquid level detecting mechanism mounted in the analyte probe 21a, and on the analyte supply information supplied from the analyte supply device 100 to the automated analyzer 1. Details of the decisions and instructions carried out by the immersion cleaning execution decision portion 44c are described next in connection with the method of automated analysis.

—Immersion Cleaning Control Portion 44d—

The immersion cleaning control portion 44d controls the drive mechanisms for the probe cleaning device 30 and the analyte dispenser 21 according to instructions from the immersion cleaning execution decision portion 44c to control immersion cleaning of the analyte probe 21a. The immersion cleaning control portion 44d carries out the immersion cleaning of the analyte probe 21a using the (1) cleaning position, (2) immersion depth, and (3) immersion time according to the operational settings for probe immersion cleaning already described in reference to FIGS. 5 and 6. The (3) immersion time is characterized in that during normal measurement operation, the immersion time is set to 2 or more cycles at which the analyte probe 21a collects analytes successively from the plural analyte receptacles P2. The immersion cleaning of the analyte probe 21a executed by the immersion cleaning control portion 44d is described in detail next in relation to the method of automated analysis.

<<Method of Automated Analysis>>

Figure 11:
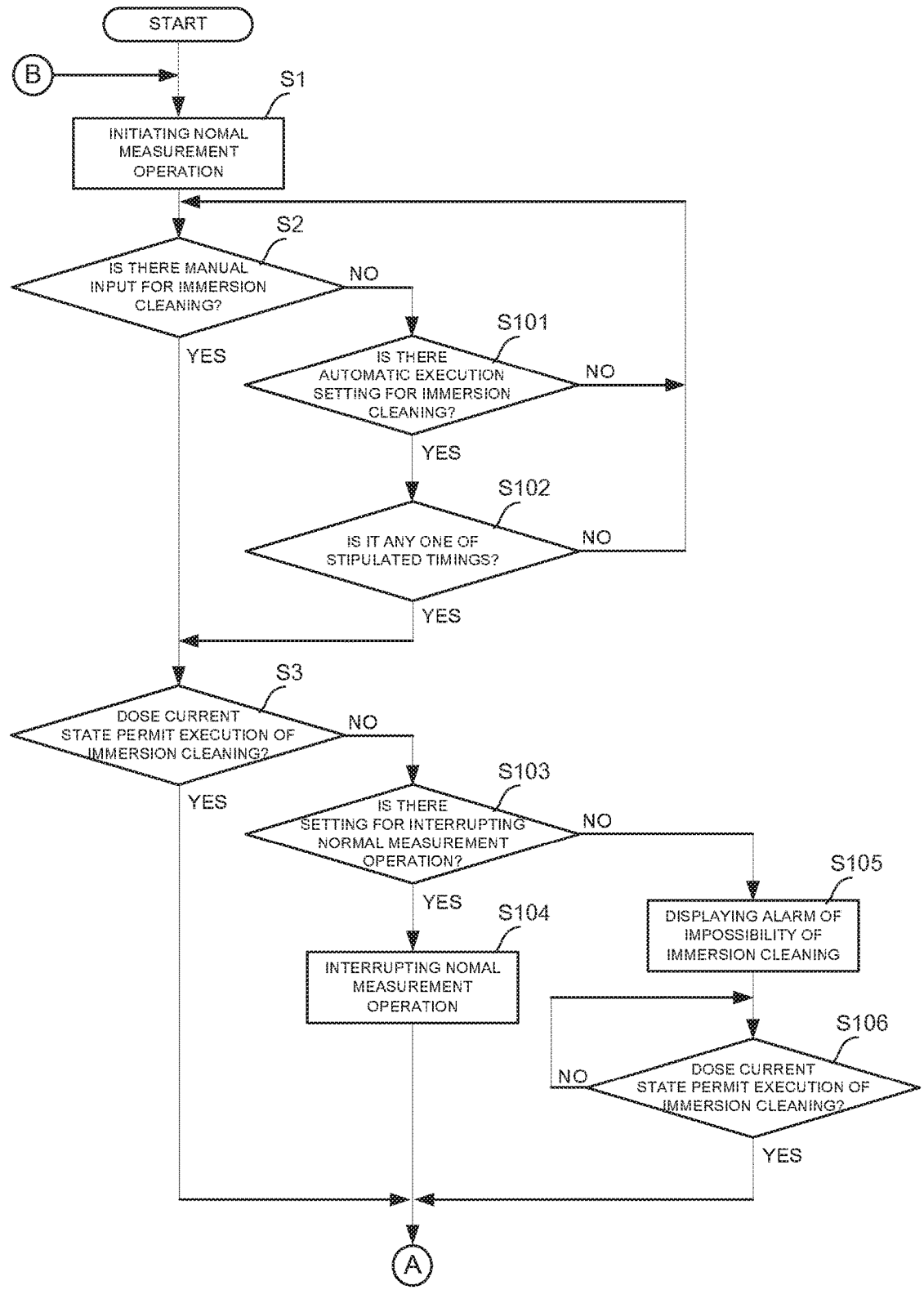
FIGS. 11 and 12 are flowcharts illustrating a method of automated analysis implemented using the automated analyzer of FIG. 1.
Figure 12:
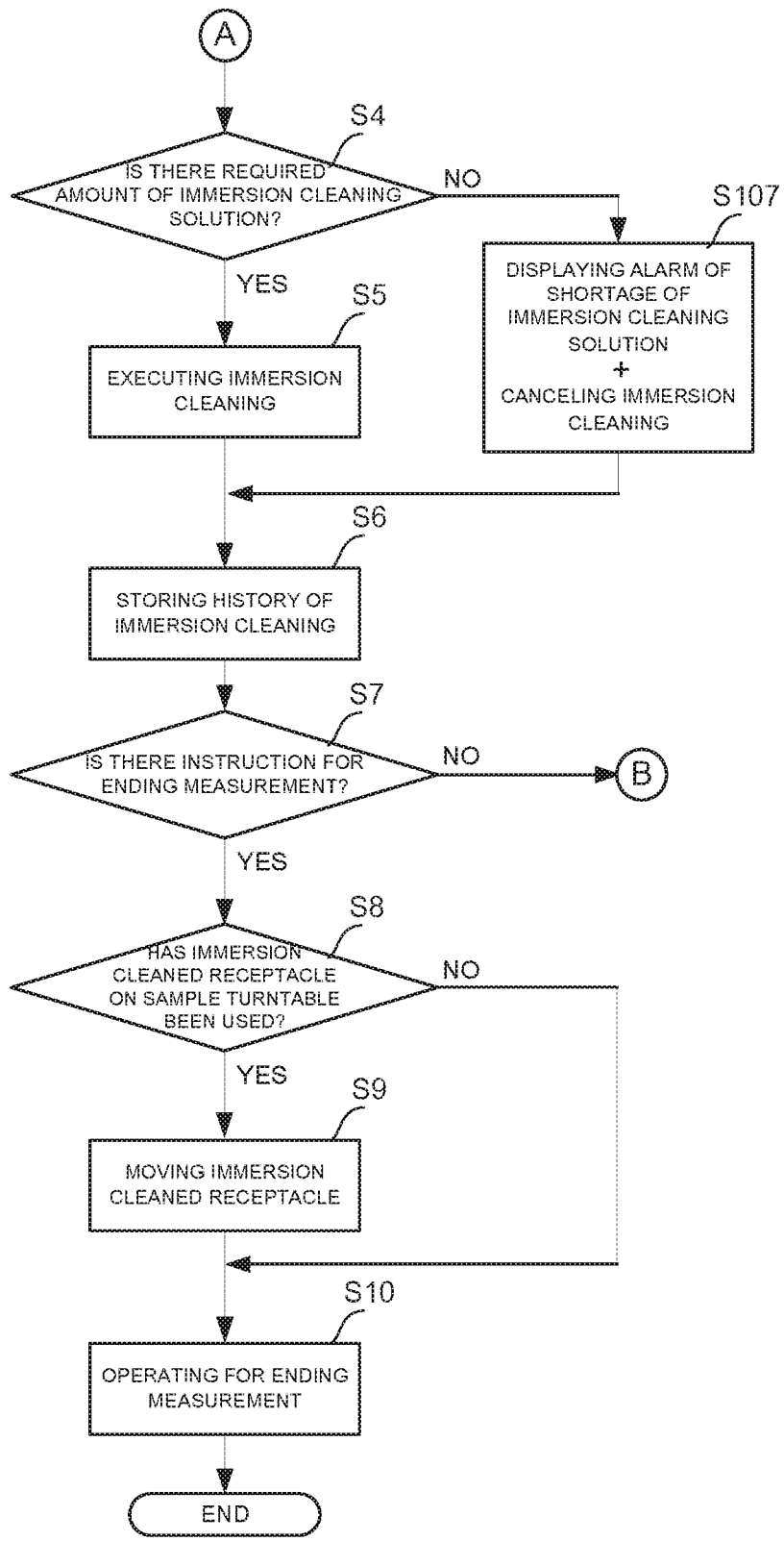

FIGS. 11 and 12 are flowcharts illustrating a method of automated analysis implemented using the automated analyzer of FIG. 1. The illustrated method of automated analysis is a series of procedures executed during the normal measurement operation or terminating operation. The analyte probe 21a is immersion cleaned for a time that is equal to 2 or more cycles of normal measurement operation. One cycle of the normal measurement operation is the period from an operation for aspirating one analyte by the analyte probe 21a to an operation for aspirating a next analyte.

These procedures are implemented by executing programs stored in the data storage section by means of the CPU constituting the input/output controller 44 already described in reference to FIG. 4. A method of automated analysis implemented by the control section 1b of the automated analyzer 1 is described hereinafter by reference to the flowcharts of FIGS. 11 and 12 in turn and also to FIGS. 1-10 as necessary.

<Step S1>

First, at step S1 illustrated in FIG. 11, the measurement control section 44b initiates a normal measurement operation under control both of the drive mechanisms for the components of the measuring section 1a and also of the multi-wavelength photometer 15.

<Step S2>

At step S2, the immersion cleaning execution decision portion 44c makes a decision as to whether there is a manual input for immersion cleaning. The immersion cleaning execution decision portion 44c makes a decision as to whether or not the operator has made a manual input of instructions for execution of immersion cleaning of the analyte probe 21a. This decision depends on, for example, whether the execution button on the manual executing setting screen for probe immersion cleaning of FIG. 7 is clicked on. If the decision is YES, indicating that there is a manual input, the immersion cleaning execution decision portion 44c determines that it is the time to execute the entered instructions for probe immersion cleaning, and control goes to step S3. On the other hand, if the decision is NO, indicating that there is no manual input, control proceeds to step S101.

<Step S101>

At step S101, the immersion cleaning execution decision portion 44c makes a decision as to whether there is an automatic execution setting for immersion cleaning. At this time, the immersion cleaning execution decision portion 44c makes a decision as to whether there is an automatic execution setting (e.g., for probe immersion cleaning as illustrated in FIG. 8) in the various setting information stored in the data storage section 43. If the decision is YES, indicating that there is an automatic execution setting, control proceeds to the next step S102. On the other hand, if the decision is NO, indicating that there is no automatic execution setting, control goes back to step S2.

<Step S102>

In step S102, the immersion cleaning execution decision portion 44c makes a decision as to whether any one of the timings stipulated respectively in the automatic execution settings (settings 1-3 of FIG. 8) for probe immersion cleaning is reached. If the decision is YES, indicating that any one timing is reached, control goes to step S3. On the other hand, if the decision is NO, indicating that any one of the timings is not reached, control goes back to step S2.

<Step S3>

In step S3, the immersion cleaning execution decision portion 44c makes a decision as to whether the current state permits execution of immersion cleaning of the analyte probe 21a. This decision is carried out based either on information about transport of the analyte into the automated analyzer 1 from the analyte supply device 100 or on analyte acceptance information possessed by the measuring control section 44b.

In this case, if there is no transport of any analyte to the automated analyzer 1 from the analyte supply device 100, it is determined that the current state permits execution of immersion cleaning of the analyte probe 21a (YES), and control goes to step S4 illustrated in FIG. 12. On the other hand, if there is a transport of an analyte into the measuring section 1a of the automated analyzer 1, and if the normal measurement operation will continue on, then the decision is NO, indicating that the current state does not allow execution of immersion cleaning of the analyte probe 21a, and control goes to step S103.

<Step S103>

In step S103, the immersion cleaning execution decision portion 44c makes a decision as to whether the various setting information stored in the data storage section 43 includes a setting for interrupting the normal measurement operation. If the decision at step S2 is YES, indicating that there is a manual input, the immersion cleaning execution decision portion 44c makes a decision as to whether the manual execution setting for probe immersion cleaning, for example, illustrated in FIG. 7 involves interruption of the normal measurement operation. On the other hand, if the decision at step S102 is YES, indicating that any one of the timings stipulated by the automatic execution setting is reached, a decision is made as to whether the setting causes an interruption of the normal measurement operation.

If the immersion cleaning execution decision portion 44c determines that there is a setting for interrupting the normal measurement operation (YES) in any one of the foregoing decision blocks, control goes to step S104. On the other hand, if the decision is NO, indicating that there is no setting for interruption of the normal measurement operation, control proceeds to step S105.

<Step S104>

In step S104, the immersion cleaning execution decision portion 44c instructs the measurement control section 44b to interrupt the normal measurement operation. In response to this, the measurement control section 44b interrupts the normal measurement operation.

<Step S105>

In step S105, the immersion cleaning execution decision portion 44c instructs the display controller 44a to produce an alarm output, indicating the impossibility of immersion cleaning. In response, the display controller 44a displays an alarm of the impossibility of immersion cleaning on the display device 41 acting as the alarm output portion. In this case, the details of the impossibility of immersion cleaning are displayed in the alarm history display screen, for example, as shown in FIG. 10, thereby providing an alarm output.

<Step S106>

In step S106, the immersion cleaning execution decision portion 44c makes a decision as to whether the current state permits execution of immersion cleaning of the analyte probe 21a, based either on information about transport of the analyte into the automated analyzer 1 from the analyte supply device 100 or on information about the acceptance of the analyte possessed by the measurement control section 44b in the same way as in step S3.

Step S106 is repeated until a YES decision occurs (i.e., it is determined that the current state permits execution of immersion cleaning), and the apparatus waits until execution of immersion cleaning is enabled. If it is determined that the current state allows execution of immersion cleaning (YES), control goes to the next step S4 illustrated in FIG. 12.

<Step S4>

In step S4, the immersion cleaning execution decision portion 44c makes a decision as to whether there is a required amount of immersion cleaning solution. At this time, the immersion cleaning execution decision portion 44c first moves the analyte probe 21a into a set cleaning position, where immersion cleaning of the analyte probe 21a is to be carried out. The set cleaning position is the (1) cleaning position stipulated by the operational setting for probe immersion cleaning already described in connection with FIGS. 5 and 6.

Where the (1) cleaning position is set on or in the probe cleaning device 30 as shown in FIG. 5, the immersion cleaning execution decision portion 44c moves the analyte probe 21a onto the immersion cleaning bath 32 of the probe cleaning device 30. If the automated analyzer 1 is equipped with a cleaned receptacle holding portion, and if the (1) cleaning position is set on the cleaned receptacle holding portion, the immersion cleaning execution decision portion 44c moves the analyte probe 21a onto the cleaned receptacle holding portion.

On the other hand, where the cleaning position (1) is set on the sample turntable as shown in FIG. 6, the immersion cleaning execution decision portion 44c moves the analyte probe 21a into the analyte collection position on the sample turntable 2. At the same time, the immersion cleaning execution decision portion 44c moves both position 1 on the sample turntable 2 and the immersion cleaned receptacle held at this position 1 into a given analyte collection position.

Then, the immersion cleaning execution decision portion 44c detects the height of the liquid level in the immersion cleaning bath 32 or in the immersion cleaned receptacle placed below the analyte probe 21a using the liquid level detecting mechanism mounted in the analyte probe 21a. The decision portion 44c then makes a decision as to whether there is a required amount of immersion cleaning solution according to the detected height of the liquid level. The required amount of immersion cleaning solution is that the immersion depth [d] of the analyte probe 21a within the immersion cleaning solution L1 is in excess of the height-wise position [A] of the analyte probe 21a immersed in the analyte within a selected one of the analyte receptacles P2 with some tolerance.

If the immersion cleaning execution decision portion 44c determines that there is a required amount of immersion cleaning solution (YES) based on the procedure described so far, control goes to step S5. On the other hand, if the decision is NO, indicating that there is no required amount of immersion cleaning solution, control proceeds to step S107.

<Step S107>

In step S107, the immersion cleaning execution decision portion 44c instructs the display controller 44a to produce an alarm output indicative of a shortage of the immersion cleaning solution. In response, the display controller 44a displays the alarm output indicative of a shortage of the immersion cleaning solution on the display device 41 that acts as the alarm output portion. In this case, the contents of the alarm output are displayed in the screen of the alarm history, for example, as shown in FIG. 10. Then, control goes to step S6.

<Step S5>

In step S5, the immersion cleaning execution decision portion 44c instructs the immersion cleaning control portion 44d to execute immersion cleaning of the analyte probe 21a. In response, the immersion cleaning control portion 44d carries out a series of steps for immersion cleaning of the analyte probe 21a. FIG. 13 is a flowchart illustrating the procedure of the immersion cleaning of the probe performed by the method of automated analysis. As illustrated in this figure, the immersion cleaning control portion 44d carries out the processing steps for immersion cleaning of the analyte probe 21a as follows.

Step S501

In step S501, the immersion cleaning control portion 44d carries out the immersion cleaning of the analyte probe 21a. At this time, the control portion 44d first lowers the analyte probe 21a. Consequently, a front end portion of the analyte probe 21a is immersed in the immersion cleaning solution L1 either within the immersion cleaning bath 32 or within the immersion cleaned receptacle to the given immersion depth [d] for a given immersion time as shown in FIG. 2. The immersion depth [d] and the immersion time are the (2) immersion depth and the (3) immersion time, respectively, of the operational setting parameters for probe immersion cleaning already described in connection with FIG. 5 or FIG. 6.

The immersion cleaning control portion 44d may vibrate the analyte probe 21a vertically or horizontally, or both, while the analyte probe 21a is kept immersed in the immersion cleaning solution L1 as previously described in order to enhance the cleaning effect of the immersion cleaning solution L1. Under this condition, the immersion cleaning control portion 44d may repeatedly aspirate and dispense the immersion cleaning solution L1 from and into the analyte probe 21a. Where the vibration of the analyte probe 21a and aspiration and delivery of the immersion cleaning solution L1 from and into the analyte probe 21a are performed, either operation may be carried out first.

This step S501 may be repeatedly carried out while replacing the immersion cleaning solution L1 inside the immersion cleaning bath 32. Where there are a plurality of immersion cleaning baths 32, the step S501 may be performed separately in the different immersion cleaning baths 32. Furthermore, the step S501 may be performed separately in different immersion cleaned receptacles. In addition, the step S501 may be performed a plurality of times in the immersion cleaning solution L1 within the immersion cleaning bath 32 or within each immersion cleaned receptacle. In any case, immersion cleaning solution L1 of the same type or different types of immersion cleaning solutions L1 may be used.

Step S502

In step S502, the immersion cleaning control portion 44d takes out the analyte probe 21a from the immersion cleaning solution L1 in the immersion cleaning bath 32 or in the immersion cleaned receptacle and moves the probe into the cleaning bath 31 of the probe cleaning device 30 located outside the immersion cleaning bath 32.

Step S503

In step S503, the immersion cleaning control portion 44d delivers a shower of rinsing liquid L2 against the analyte probe 21a inside the cleaning bath 31 from the cleaning solution supply tube 33 to rinse out the analyte probe 21a. At this time, the cleaning solution supply tube 33 supplies the rinsing liquid L2 to the analyte probe 21a from a position higher than the heightwise position [B] at which the tip of the analyte probe 21a is immersed in the immersion cleaning solution L1 during immersion cleaning as shown in FIG. 3.

Furthermore, the immersion cleaning control portion 44d ejects water from inside the analyte probe 21a into the cleaning bath 31 and washes out the inner wall of the analyte probe 21a.

Step S504

In step S504, the immersion cleaning control portion 44d brings the analyte probe 21a out of the cleaning bath 31.

Step S505

In step S505, the immersion cleaning control portion 44d makes a decision as to whether the immersion cleaning bath 32 has been used for immersion cleaning of the analyte probe 21a. If the immersion cleaning executed in step S501 is carried out in the immersion cleaning bath 32, the control portion 44d determines that the immersion cleaning bath 32 has been used (YES) for probe immersion cleaning, and control goes to step S506.

On the other hand, if the immersion cleaning performed at step S501 is carried out in an immersion cleaned receptacle held either to the sample turntable 2 or to the cleaned receptacle holding portion, the immersion cleaning control portion 44d determines that the immersion cleaning bath 32 has not been used for the immersion cleaning (NO), and a series of processing steps of the immersion cleaning is ended. Control then proceeds to step S6 illustrated in FIG. 12.

Step S506

In step S506, the immersion cleaning control portion 44d overflows the immersion cleaning solution L1 inside the immersion cleaning bath 32 and replaces the solution. Then, the series of processing steps of immersion cleaning is ended. Control then goes to step S6 illustrated in FIG. 12.

If information about the transport of an analyte from the analyte supply device 100 to the automated analyzer 1 or information about the acceptance of an analyte from the measurement control section 44b arrives amidst the aforementioned series of processing steps of immersion cleaning, the immersion cleaning execution decision portion 44c causes the measurement control section 44b to suspend the initiation of the normal measurement operation and brings the measurement control section 44b to a halted state until the processing for immersion cleaning is ended.

<Step S6>

In step S6, the immersion cleaning execution decision portion 44c instructs the data storage section 43 to store the history of immersion cleaning. Consequently, when immersion cleaning of the analyte probe is carried out or canceled, the history of circumstances of the execution are stored in the data storage section 43 together with date and time information and the contents of an instruction for the execution, for example, as illustrated in FIG. 9.

<Step S7>

In step S7, the immersion cleaning execution decision portion 44c makes a decision as to whether there is an instruction for ending the measurement based on information from the measurement control portion 44b. If the decision is YES, indicating that there is an instruction for ending the measurement, control goes to step S8. On the other hand, if the decision is NO, indicating that there is no instruction for ending the measurement, control goes back to step S1 illustrated in FIG. 11 and the normal measurement operation is resumed.

<Step S8>

In step S8, the immersion cleaning execution decision portion 44c makes a decision as to whether an immersion cleaned receptacle on the sample turntable 2 has been used for immersion cleaning of the analyte probe 21a. If the immersion cleaning included in the immersion cleaning processing of step S5 has been carried out in the immersion cleaned receptacle on the sample turntable 2, the immersion cleaning execution decision portion 44c determines that an immersion cleaned receptacle has been used (YES), and control goes to step S9. On the other hand, if the immersion cleaning at step S5 has been carried out in an immersion cleaned receptacle held either in the immersion cleaning bath 32 or to the cleaned receptacle holding portion, the immersion cleaning execution decision portion 44c determines that the immersion cleaned receptacle on the sample turntable 2 has not been used (NO), and control proceeds to step S10.

<Step S9>

In step S9, the immersion cleaning execution decision portion 44c moves the immersion cleaned receptacle on the sample turntable 2, which has been used in the immersion cleaning processing of step S5, into a given receptacle take-out position. This permits the operator to take out the immersion cleaned receptacle receiving the immersion cleaning solution L1 from the sample turntable 2 before the end of the measurement. Then, control goes to step S10.

<Step S10>

In step S10, the immersion cleaning execution decision portion 44c causes the measurement control portion 44b to perform a given operation for ending the measurement, thus terminating a series of processing steps for automated analysis.

Advantageous Effects of Embodiments

According to the embodiments described so far, immersion cleaning of the analyte probe 21a in which the analyte probe 21a is immersed in the immersion cleaning solution L1 is carried out for a time as long as two or more cycles of the normal measurement operation. Therefore, contamination adhering to the analyte probe 21a can be effectively removed without using a sweeping cleaning member. As a result, the running costs of the automated analyzer 1 can be reduced. Also, carryover of analytes and thus their contamination can be prevented. Hence, the accuracy of measurement can be enhanced.

Modified Embodiments

In the embodiments described so far, if the decision at step S4 is NO, indicating that there is not a required amount of immersion cleaning solution, the immersion cleaning of the analyte probe 21a is canceled. However, if the (1) cleaning position is in the immersion cleaning bath 32 of the probe cleaning device 30 as illustrated in FIG. 5, the decision at step S4 is NO, indicating that there is not a required amount of immersion cleaning solution. Then, the immersion cleaning execution decision portion 44c may supply a required amount of immersion cleaning solution L1 from the immersion cleaning solution supply tube 32a into the immersion cleaning bath 32, and then control may go to step S5. If the (1) cleaning position is either on the sample turntable 2 or in an immersion cleaned receptacle held to the cleaned receptacle holding portion as illustrated in FIG. 6, the immersion cleaning execution decision portion 44c may wait until the operator adds further immersion cleaning solution L1 into the immersion cleaned receptacle, and then control goes to step S5.

Furthermore, in the embodiments described so far, the probe cleaning device 30 for cleaning the analyte probe 21a has the immersion cleaning bath 32. However, the probe cleaning device 30 may not have the immersion cleaning bath 32, in which case immersion cleaning of the analyte probe 21a may be carried out by the immersion cleaning solution L1 in the immersion cleaned receptacle held either on the sample turntable 2 or in the cleaned receptacle holding portion.

In addition, in the description of the embodiments described so far, immersion cleaning of the analyte probe 21a is exemplified as immersion cleaning of a dispensing probe. However, immersion cleaning of a dispensing probe by the method of automated analysis of the present invention is not restricted to an analyte probe but rather applied to a wide variety of other types of dispensing probes.

Additionally, in the above embodiments, the manual execution setting for probe immersion cleaning as illustrated in FIG. 7 and the automatic execution setting for probe immersion cleaning as illustrated in FIG. 8 can both be used. However, in immersion cleaning of a dispensing probe by the method of automated analysis of the present invention, the timing of execution of immersion cleaning of a dispensing probe may be set using only one of the two settings.

Further, in the embodiments described so far, prior to execution of the cleaning operation of step S5, the execution of the cleaning operation may be allowed to be canceled by an operator's manual input through the input section 42. One example of this configuration is to add a cancel input decision step for making a decision as to whether an instruction for canceling immersion cleaning has been manually entered. The cancel input decision step is placed in at least one position: (a) between steps S3 and S4, (b) between steps S105 and S106, (c) between steps S104 and S4, and (d) from the start of step S4 to the end of step S5.

Where cancel input decision steps are added at the points (a) and (b) above, if it is determined that an instruction for canceling immersion cleaning has been manually entered (YES), control goes back to step S2.

Where a cancel input decision step is added at the point (c) above, if the decision is YES, indicating that an instruction for canceling immersion cleaning has been manually entered, it follows that the normal measurement operation is interrupted at the immediately preceding step S104. Therefore, control goes back to step S1.

Where a cancel input decision step is added at the point (d) above, if the decision is YES, indicating that an instruction for canceling immersion cleaning has been manually entered, there is the possibility that the tip of the probe may be immersed in a cleaning solution at the immediately preceding step S4. Therefore, after execution both of rinsing of the probe and of exchange of the overflowing immersion cleaning solution, control goes back to step S1. In this case, it suffices to carry out steps S502-S506 already described in connection with FIG. 13. Then, control goes back to step S1.

On the other hand, where the cancel input decision step is added at the points (a)-(d) above, if the decision is NO, indicating that any instruction for canceling immersion cleaning is not manually entered, control may proceed to the next step.

Where the aforementioned instruction for canceling immersion cleaning is manually entered, the history of cancellations of immersion cleaning of the analyte probe in response to manual inputs may be stored, for example, in the immersion cleaning execution decision portion 44c.

The invention claimed is:

1. An automated analyzer comprising:
a measuring section comprising:
a receptacle holding portion for holding a plurality of receptacles in which analytes are stored as aliquots of liquid;
an immersion cleaning solution holding portion for storing an immersion cleaning solution; and
an analyte dispenser equipped with a drive mechanism for holding a dispensing probe operative to collect the analytes from the receptacles held to the receptacle holding portion such that the dispensing probe can be moved between the receptacle holding portion and the immersion cleaning solution holding portion;

a measurement controller configured to control the drive mechanism of the analyte dispenser and the dispensing probe to successively collect the analytes at given cycles from the receptacles held to the receptacle holding portion;

an immersion cleaning controller configured to control the drive mechanism of the analyte dispenser and the dispensing probe to execute an immersion cleaning operation comprising immersing the dispensing probe in the immersion cleaning solution stored in the immersion cleaning solution holding portion for an immersion time that is at least twice as long as a period of each of the given cycles; and an immersion cleaning execution decision portion configured to:

determine a current state of the automated analyzer based on whether a new analyte is being transported into the measuring section;

in response to determining the current state indicates the new analyte is not being transported into the measuring section, determine that the immersion cleaning operation is executable and instruct the immersion cleaning controller to carry out the immersion cleaning operation; and in response to determining the current state indicates the new analyte is being transported into the measuring section, determine that the immersion cleaning operation is inexecutable and prioritize normal measurement operations.

2. The automated analyzer as set forth in claim 1, further comprising an input section for entering a timing of said immersion cleaning operation, and wherein said immersion cleaning execution decision portion is further configured to determine that said immersion cleaning operation is executable in response to a determination that the current state indicates the new analyte is not being transported into the measuring section at said timing.

3. The automated analyzer as set forth in claim 1, further comprising an input section for entering a timing of said immersion cleaning operation of said dispensing probe, and wherein said immersion cleaning execution decision portion is further configured to cause said immersion cleaning controller to suspend said immersion cleaning operation in response to a determination that the current state indicates the new analyte is not being transported into the measuring section at said timing of said immersion cleaning operation, until the immersion cleaning operation is determined to be executable.

4. The automated analyzer as set forth in claim 1, further comprising an alarm output portion for producing an alarm output in response to said immersion cleaning execution decision portion determining that said immersion cleaning operation is inexecutable.

5. The automated analyzer as set forth in claim 1, further comprising a probe cleaning bath having a cleaning solution supply tube and mounted in a trajectory or path of movement of said dispensing probe, and wherein said immersion cleaning controller controls said drive mechanism to move the dispensing probe into the probe cleaning bath after said immersion cleaning operation such that the dispensing probe is cleaned with a cleaning solution supplied from the cleaning solution supply tube.

6. The automated analyzer as set forth in claim 5, wherein said cleaning solution supply tube is disposed on top of said probe cleaning bath and supplies a shower of the cleaning solution onto the dispensing probe disposed inside the probe cleaning bath.

7. The automated analyzer as set forth in claim 5, wherein said immersion cleaning solution holding portion is an immersion cleaning bath mounted inside said probe cleaning bath.

8. The automated analyzer as set forth in claim 1, wherein a cleaned receptacle holding portion for holding receptacles where the immersion cleaning solution is stored is mounted as said immersion cleaning solution holding portion in a trajectory or path of movement of said dispensing probe.

9. The automated analyzer as set forth in claim 1, wherein said immersion cleaning controller controls said drive mechanism to vibrate said dispensing probe within said immersion cleaning solution during said immersion cleaning operation.

10. The automated analyzer as set forth in claim 1, wherein said immersion cleaning controller controls said drive mechanism to repetitively aspirate and dispense said immersion cleaning solution from and into said dispensing probe during said immersion cleaning operation.

11. A method of automated analysis implemented by an automated analyzer having a measuring section comprising: a receptacle holding portion for holding a plurality of receptacles in which analytes are stored as aliquots of liquid; an immersion cleaning solution holding portion for storing an immersion cleaning solution; and an analyte dispenser equipped with a drive mechanism for holding a dispensing probe operative to collect the analytes from the receptacles held to the receptacle holding portion such that the dispensing probe can be moved between the receptacle holding portion and the immersion cleaning solution holding portion; said method of automated analysis comprising the steps of:

controlling said drive mechanism of the analyte dispenser and said dispensing probe such that the analytes are successively collected at given cycles from the receptacles held to the receptacle holding portion;

controlling the drive mechanism of the analyte dispenser and the dispensing probe such that an immersion cleaning operation in which the dispensing probe is immersed in the immersion cleaning solution stored in the immersion cleaning solution holding portion is carried out for an immersion time that is at least twice as long as the period of each of the given cycles;

determining a current state of the automated analyzer based on whether a new analyte is being transported into the measuring section;

in response to determining the current state indicates the new analyte is not being transported into the measuring section, determining the immersion cleaning operation is executable and carrying out the immersion cleaning operation; and in response to determining the current state indicates the new analyte is being transported into the measuring section, determining that the immersion cleaning operation is inexecutable and prioritizing normal measurement operations.

* * * * *